(12) United States Patent
Blume

(10) Patent No.: US 7,053,391 B2
(45) Date of Patent: May 30, 2006

(54) APPARATUS FOR CONVERTING A STANDARD DENTAL X-RAY VIEWBOX INTO AN ANALOG OR DIGITAL VIEWING SYSTEM

(76) Inventor: Stephen Thomas Blume, 25462 Wagon Wheel Cir., Laguna Hills, CA (US) 92653

( * ) Notice: Subject to any disclaimer, the term of this patent is extended or adjusted under 35 U.S.C. 154(b) by 112 days.

(21) Appl. No.: 10/920,402

(22) Filed: Aug. 18, 2004

(65) Prior Publication Data
US 2006/0038141 A1    Feb. 23, 2006

(51) Int. Cl.
*H05G 1/44*    (2006.01)
(52) U.S. Cl. ............... 250/559.02; 378/38; 378/167
(58) Field of Classification Search ........... 250/559.02, 250/559.29; 378/38–40, 167, 168, 170
See application file for complete search history.

(56) References Cited

U.S. PATENT DOCUMENTS 5,386,448 A * 1/1995 Tammisalo et al. ........... 378/38
5,562,448 A * 10/1996 Mushabac ................... 433/215
6,947,038 B1 * 9/2005 Anh et al. ................... 345/419
2004/0190678 A1 * 9/2004 Rotondo et al. .............. 378/38

* cited by examiner

Primary Examiner—Stephone B. Allen

(57) ABSTRACT

An apparatus that mounts on a standard dental x-ray film view box, and holds a moveable camera chassis with a high resolution CCD video board camera therein, is disclosed. The advantage of this invention is that users will be able to quickly, easily, and inexpensively convert a standard dental x-ray viewer into analog and/or digital x-ray image viewing systems, utilizing computer or video monitors. The camera chassis with CCD video board camera is mounted on tracks set on a line disposed to be parallel to both the X-axis and Y-axis of the plane of the translucent viewing plate of a standard dental x-ray viewer. The CCD video camera can slide over a target x-ray film placed thereon, for selective viewing on a video monitor or computer monitor. Additionally, the CCD video camera mechanism can be rotated up and away from the x-ray film set, which allows the dentist to visually scan the entire x-ray film set without visual obstruction. Users will also be able to utilize this device for enhanced diagnosis, and to show greatly enlarged and high resolution x-ray film images to patients for education and improved case presentation.

7 Claims, 3 Drawing Sheets

APPARATUS FOR CONVERTING A STANDARD DENTAL X-RAY VIEWBOX INTO AN ANALOG OR DIGITAL VIEWING SYSTEM

BACKGROUND OF THE INVENTION

Around 1900 radiographs were just starting to be utilized in the medical, dental, veterinary, and other health related fields. This new technology greatly aided the health practitioner in diagnosing disease and injury of the hard tissues. In more recent years, radiographs, with the aid of other diagnostic techniques, have been helpful in soft tissue diagnosis. Radiographic film (x-ray film) has gone through several evolutionary changes to improve resolution and dynamic range, reduce fogging, and increase speed (thereby requiring less x-ray exposure). Through years of clinical usage, film based radiography has become the gold standard as a diagnostic aid for health care professionals throughout the world.

In the case of medical radiology, films utilized are very large, making diagnosis and diagnostic presentation to a patient, by direct viewing, a comparatively simple task. Even in the case of dental orthodontic film, since the entire head is usually radiographed on 8"×10" film, case presentation is not a difficult process. However, in the case of general dentistry, and most dental specialties, intra-oral dental film is used. By necessity, such films must be quite small in order to place the film inside of the patients' mouth. Further, the objects being radiographed, the patients' teeth, are small. The net result is that dental x-ray film and images thereon are exceedingly small, making diagnosis and patient case presentation utilizing these x-ray films a difficult task. After x-rays films are exposed on the patient in the dental office, then processed, the dentist must examine them in order to determine if there are ailments to be treated. Thus, the dentist may identify dental caries by noting dark (radiolucent) areas on the x-ray image. The dentist also checks the bone density and levels, examines the roots and nerves of the teeth, checks the position and development of the teeth, looks for lesions such as cysts or tumors, assesses damage when trauma occurs, and monitors periodontal conditions. All of this must be determined on a set of very small film, each of which is approximately an inch by an inch and a half round-cornered rectangle. The conventional way in which this is done is to clip the film to a dental x-ray viewer light box, (hereinafter denoted x-ray viewer) which acts as an aid in the inspection of the x-ray film. The dentist can then visually scan the entire x-ray set and render a diagnosis.

Several attempts have been made to make x-ray reading a less difficult endeavor. A variety of magnifying glass-type devices have been utilized when viewing film. This technique has been moderately successful, aiding the dentist in diagnosis. However, the patient is generally unable to view the film with the dentist, making discussion and case presentation difficult.

Another attempt to display x-ray images on a screen is a technique called direct digital imaging. This technique involves utilizing an x-ray sensing charged coupling device (CCD) that is placed in a patient's mouth then exposed to a small dose of x-rays. An image formed on the CCD device is directly sent to a computer where it is digitized. The image can then be viewed on a computer screen, and can be manipulated and printed. To date, this is an exceedingly expensive technique. Further, it is ergonomically awkward because of the fact that all x-ray images to be viewed are on a computer disk. Film sets cannot be visually scanned by the dentist. After booting up the computer, the operator must select the patient's file, and then "click" on each film to be viewed. Further, digital images do not have the image clarity and quality of film.

Another variation of this technique utilizes phosphur-covered sensors that are sensitive to x-rays. These sensors are placed in the patients' mouth, then exposed to x-rays. The sensors are then transferred to a reading device which captures the image from the sensor and sends it to a computer for digitizing. The drawbacks for this technique are the same as those of direct digital imaging.

PRIOR ART

Several inventors have described other techniques that attempt to alleviate the problems associated with dental x-ray film and image manipulation and viewing. Samuel Zimmerman (U.S. Pat. No. 4,013,833) describes x-ray film images projected onto a target plate such as a vidicon, in a video camera of the type used in closed video systems. He further describes a video camera means for capturing images from x-ray films. Richard d. Beer, et al, (U.S. Pat. No. 5,995,138) describes capturing the image from dental x-ray film through the use of a video camera. The image is sent to a computer to be digitized, for the purpose of aiding communication between dentists and insurance companies. The film is placed, unmounted, one by one, in a slot so that it may pass by a video camera for image capture.

Capturing images from dental x-ray film and sending these images to a video monitor or computer monitor is an excellent method of displaying and reading x-ray films. This technique provides an excellent image that may be utilized for both diagnosis and patient case presentation. The inability of this idea to be successfully marketed relates to the complexity, poor ergonimics, and cost of the overall systems as previously disclosed.

In order to capture an image from dental x-ray film and send it to a video monitor, there are five items required: (1) a backlighted translucent plate (as on an x-ray viewer) (2) film to be viewed laid over the translucent viewing plate (3) a mounted focused video camera in proper focal length from the target x-ray film (4) a video cable utilized to send the captured image to (5) a video monitor or computer configured to accept an analog image. There are two common types of x-ray film viewers utilized by dentists today: wall mounted viewers, and desktop viewers. There are literally hundreds of thousands of these x-ray viewers already in use by dentists as of this writing. Further, about half of all dentists utilize intra-oral cameras in their offices, which show a patient an enlarged color image of their teeth, and maladies thereof, on a video monitor. A majority of dentists have (1),(2), and (4) above and therefore already have most of the equipment needed to pick up images from x-ray film, and send them to electronic monitors. Clearly, a simple and inexpensive device that would allow for the mounting of a moveable high resolution CCD video camera on existing x-ray viewers, and the sending of the images captured to existing video and/or computer monitors, would greatly enhance a dentists ability to educate, and to communicate case presentation to his patients, and improve the dentist's diagnostic abilities. If there were an apparatus such as this, which would inexpensively and quickly convert a standard x-ray viewer into an analog/digital imaging system, the idea of capturing images from dental x-rays with a CCD video camera for diagnosing and patient case presentation could become commercially successful and commonplace.

SUMMARY OF THE INVENTION

Standard dental x-ray viewers are universally composed of a rectangular-shaped chassis "box", a front white translucent plate configured to hold a target x-ray film set, and one or more 110 volt fluorescent bulbs beneath the viewing plate. Any references to a standard x-ray viewer or the parts thereof will, for the purposes of this disclosure, mean a dental x-ray viewer that the apparatus of this disclosure will be mounted upon. In accordance with the preferred embodiment of the present invention, an apparatus is disclosed that will easily and efficiently allow for the mounting of a moveable high resolution CCD video camera to any standard dental x-ray viewer, thereby converting this x-ray viewer into an analog/digital video x-ray image viewing system.

As such, there is provided a camera housing configured to have a high resolution CCD video board camera and lens mounted therein. Further, the CCD video camera housing is configured with two through holes which are parallel to the Y-axis of the plane of the CCD plate coupled to the video camera board mounted therein. These holes, having a larger diameter than the rod-shaped tracks that will support the camera housing over target x-ray film, will allow the camera housing to slide freely over the translucent plate. The camera housing further has a quarter inch thick ruby-clear acrylic filter over the lens-end of the housing. The brightness of the lighted viewing plate of virtually all dental x-ray viewers is far too bright for the electronic iris of most CCD video cameras at the close range required for reading dental x-rays. Reducing this light through the use of a ruby-clear acrylic filter will greatly improve electronic iris functioning. The camera housing is additionally configured with an indicator light, and a wire cable with strain relief for the purpose of bringing power to the CCD video camera and outputting the video image.

Supporting the camera housing, with CCD video camera mounted therein, are two rod-shaped tracks, configured to be parallel to the Y axis of the translucent plate. For the purpose of this disclosure, tracks configured to be parallel to the Y axis of target x-ray film and translucent plate shall herein be denoted "Y-axis tracks". These tracks are joined at their lower extension by a cross member that rests on the lower chassis of the x-ray viewer. This cross member helps to support the camera housing so that the CCD video camera is in good focal length from target x-ray film.

The upper ends of the Y-axis tracks are mechanically coupled with a carrier composed of a solid low friction plastic material such as nylon or delrin. This carrier is further disposed to slide in a direction that is parallel to the X-axis of the translucent plate, carrying the camera housing and Y-axis tracks on a single rod shaped track which is disposed to be on a line parallel to the X-axis of the plane of the translucent viewing plate. This track shall be denoted "X-axis track" for the purposes of this disclosure.

Additionally, on the side of the camera housing at the level of and perpendicular to a Y-axis track, and parallel to the translucent viewing plate, there is configured a tapped through-hole with threaded locking knob screwed therein. This locking knob is capable of being tightened against the Y-axis track, thereby allowing the user to selectively lock the camera housing on the Y-axis track. The affect of this chassis lock is to hold the CCD video camera in place for the viewing of any individual x-ray film at all levels on a target film set.

There is further provided an upper left attachment member and an upper right attachment housing configured so that the attachment member and attachment housing will conform to and attach to the upper right and left front of the chassis of a standard dental x-ray viewer. In the preferred embodiment, the attachment member and attachment housing are mounted to the x-ray viewer by utilizing double-sided adhesive pads such as those manufactured by 3M Corp. The attachment member and attachment housing are hollow rectangular box-shaped blocks with flat sides which act as an aid in holding the attachment member and attachment housing to the dental x-ray viewer chassis on the flat upper right and left front surface via the double sided adhesive pad. The attachment housing, being hollow, has: (1) a socket configured to accept the incoming 12 volt DC power source for the CCD video camera and indicator light; (2) a socket configured to accept connection with the cable which carries outgoing video images. to a video monitor, or to a computer; (3) a multi-wire cable, with strain relief bushing, that carries power to the CCD video camera from the attachment housing, and carries the x-ray image back to the video socket in the attachment housing; and, (4) a power switch.

In the preferred embodiment, disposed between the attachment member and attachment housing is the rod shaped X-axis track discussed above. This X-axis track, when the camera housing, the attachment member, and attachment housing are mounted on the x-ray viewer, is situated far enough above the translucent viewing plate so that the CCD video camera will be able to slide upward and be centered over the highest film of a target x-ray film set. Further, the X-axis track is adjustably imbedded into the attachment member and attachment housing in such a way that the length of the X-axis track can be modified by moving the attachment member and attachment housing on the X-axis rod as required for mounting on the variety of different brands of x-ray viewers available. Radiography equipment manufacturing companies make dental x-ray viewers with differing lengths and heights of translucent plates and chassis, and all of these variations must be accommodated. For example, Clive Craig Inc. makes a viewer that has a 12⅞ inch by 4¹³⁄₁₆ inch translucent viewing plate. Star Dental Inc. makes a plate that is 14⅛ inches by 5³⁄₁₆ inches. Dentsply Inc. makes a viewing plate that is 12 inches by 6 inches. The device of the present invention must be constructed so that it will be mountable on all of the various manufactured dental x-ray viewers.

An advantage of the present invention is that it will allow dentists to quickly, simply, and inexpensively mount a moveable high resolution CCD video camera on a standard dental x-ray viewer so that they may view large, high-resolution, x-ray film images of ordinary x-ray film on a video monitor for case presentation and diagnosis An additional advantage of the present invention is that a dentist can inexpensively and simply have a high-resolution digital x-ray viewing system through the use of a computer with video capabilities.

An additional advantage of the present invention is that the housing utilized to mount the apparatus on an x-ray viewer carries all wiring necessary to power the CCD video camera and camera housing electronics.

A further advantage of the present invention is that the housing utilized to mount the apparatus on the dental x-ray viewer has an input from the video camera that carries the image from target dental x-ray film.

An additional advantage of the present invention is that the lens opening of the camera chassis is covered by a ruby-clear acrylic filter which reduces the excessive light going into the CCD video camera which may overwhelm the CCD video camera iris.

A further advantage of the present invention is that the video mechanism can be rotated and lifted out of the way of the x-ray viewing plate so that the target x-ray film can be fully viewed directly by the operator.

A BRIEF DESCRIPTION OF THE DRAWINGS

These as well as other features of the present invention will become more apparent upon references to the drawings wherein.

DETAILED DESCRIPTION OF THE PREFERRED EMBODIMENT

Figure 1:
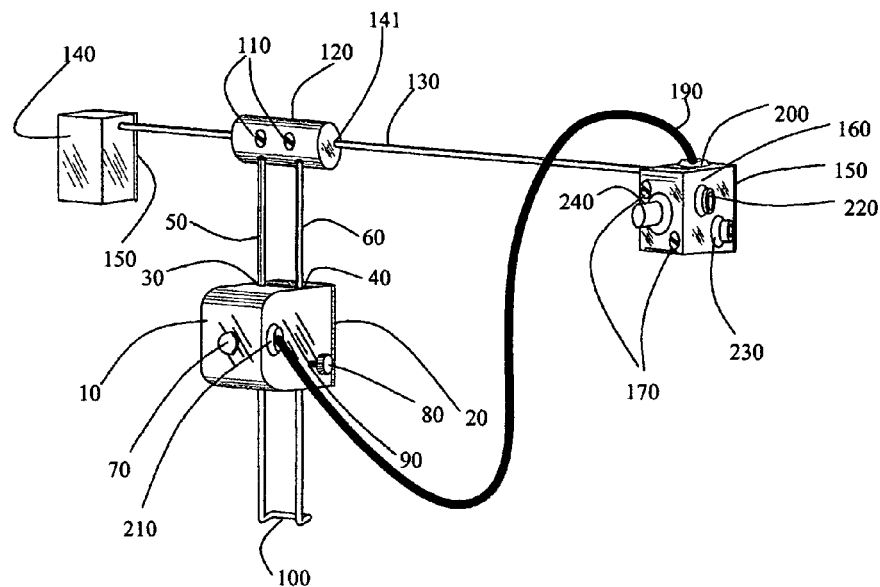
FIG. 1 is a perspective view of the CCD video camera mounting apparatus independent of a dental x-ray viewer.

Referring now to the drawings wherein the showings are for the purposes of illustrating a preferred embodiment of the present invention only, and not for the purposes of limiting the same, FIG. 1 perspectively illustrates the CCD video camera mounting apparatus constructed in accordance with the preferred embodiment of this invention. Camera housing (10) defines a top wall, bottom wall two side walls, and a back wall which acts as a housing utilized both for mounting a CCD video board camera therein, and as a hand holder which allows the operator to move said camera housing and CCD video camera in both the X-axis and Y-axis directions over the plane of the translucent viewing plate. Camera housing (10), in the preferred embodiment, is constructed of a plastic material. The side facing target x-ray film is open allowing the lens of the CCD video camera viewing access to target x-ray film images. Due to the close proximity of said CCD video camera and lens to the brightly lit translucent viewing plate of the dental x-ray viewer, ruby-clear acrylic filter (20) covers the opening of camera housing (10) which faces the x-ray viewer transparent plate. Through holes (30) and (40) have a diameter that is configured to be just larger than Y-axis tracks (50) and (60), which will allow camera housing (10) to slide freely on a line which is parallel to the Y axis of the plane of target x-ray film on the translucent viewing plate. In the preferred embodiment, Y-axis tracks (50) and (60) are constructed of quarter inch stainless steel rods.

Indicator light (70) allows the operator to know when said CCD video camera board within camera housing (10) is powered and in operational mode. Chassis locking knob (80) will allow camera housing (10) to be selectively locked on Y-axis tracks (50) and (60). Threaded through hole (90) in camera housing (10) is in communication with Y-axis track (60). To hold camera housing (10) in place, locking knob (80) is tightened. The affect of locking knob (80) is to allow camera housing (10) with CCD video camera therein to be selectively held in position over films on any row of a mounted x-ray set. Further, anterior x-ray films are mounted with the long dimension positioned parallel to the Y-axis of the translucent plate. Since all video monitors have screens with the length parallel to the X-axis of target x-ray film, the entire film cannot be displayed in one view. Locking knob (80) will allow the operator to lock camera housing (10) in position with a view of the lower portion of the target x-ray film, then to slide the camera housing slightly upward for a viewing of the upper portion of the x-ray film. The lower extensions of tracks (50) and (60) are supported on the viewer chassis by lower cross member (100). Cross member (100) is "U" shaped and is configured to slide on the lower chassis of an x-ray viewer on a line parallel to the X-axis of the plane of the translucent viewing plate. In the preferred embodiment, cross member (100) is disposed to act as a lower stop for camera housing (10). The length of Y-axis tracks (50) and (60) is adequate to allow the operator to adjust and mount the apparatus on any height of standard x-ray viewer on the market. Lock screws (110) communicate with Y-axis tracks (50) and (60). When mounting the apparatus of this disclosure on an x-ray viewer, cross member (100) is set at the center of the lower dental x-ray viewer chassis, track lengths are adjusted, and lock screws (110) are tightened.

The upper extension of Y-axis tracks (50) and (60) are adjustably attached into upper carrier (120). Upper carrier (120) is constructed of a rod shaped low friction plastic material such as 1-inch diameter nylon or delrin. Upper carrier (120) is configured to slide on X-axis track (130). X-axis track (130) is configured to be parallel to the X-axis of the plane of the translucent viewing plate. As such, upper carrier (120) is configured with through hole (141) that is also parallel to the X axis of the translucent viewing plate. The diameter of through hole (141) is just larger than the diameter of X-axis track (130), which will allow free movement of upper carrier (120) with camera chassis (10) in a direction that is parallel to the X-axis of the translucent viewing plate. Further, X-axis track (130) is constructed of quarter inch stainless steel rod.

In the preferred embodiment, the left extension of X-axis track (130) is adjustably joined with attachment member (140), which has the configuration of a rectangular six-sided box, and is composed of a plastic material. The flat surface of said mounting member allows for the adhesive attachment to the flat front surface of the dental x-ray viewer via double-sided adhesive pads (150).

Additionally, there is configured on the right extension of X-axis track (130) an attachment housing (160) into which X-axis track (130) is adjustably joined. Said attachment housing acts as both the confluence of all electronic couplings of the present invention, and as an attachment means. As such, in the preferred embodiment, attachment housing (160) is constructed of a plastic material which has the configuration of a rectangular six-sided box. The flat surface of attachment housing (160) allows for the adhesive mounting to the upper right front flat surface of said x-ray viewer via double-sided adhesive pads (150).

The side of attachment housing (160) away from said x-ray viewer chassis is openable. Removing screws (170) will give internal access which allows for wire soldering and socket connection therein. Attachment housing (160) is joined to the CCD video camera inside camera housing (10) by cable (190). Cable (190) is electronically coupled with the CCD video camera, and the power connector and video connector mounted on attachment housing (160). Cable (190) carries both positive and negative 12-volt DC lines, as well as video cable and a ground as needed to operate both the CCD video camera, and indicator light (70). Cable (190) enters attachment housing (160) via panel strain relief bushing (200). Additionally, cable (170) enters camera housing (10) through strain relief bushing (210). Attachment housing (160) has power socket (220) which allows for the connection of a 12 volt DC power supply. Further, attachment housing (160) has RCA socket (230) which allows for the connection of an external video cable which transfers an x-ray image to a computer or video monitor. Power switch (240) is utilized to selectively turn the CCD video camera and indicator light (70) "on" and "off".

Figure 2:
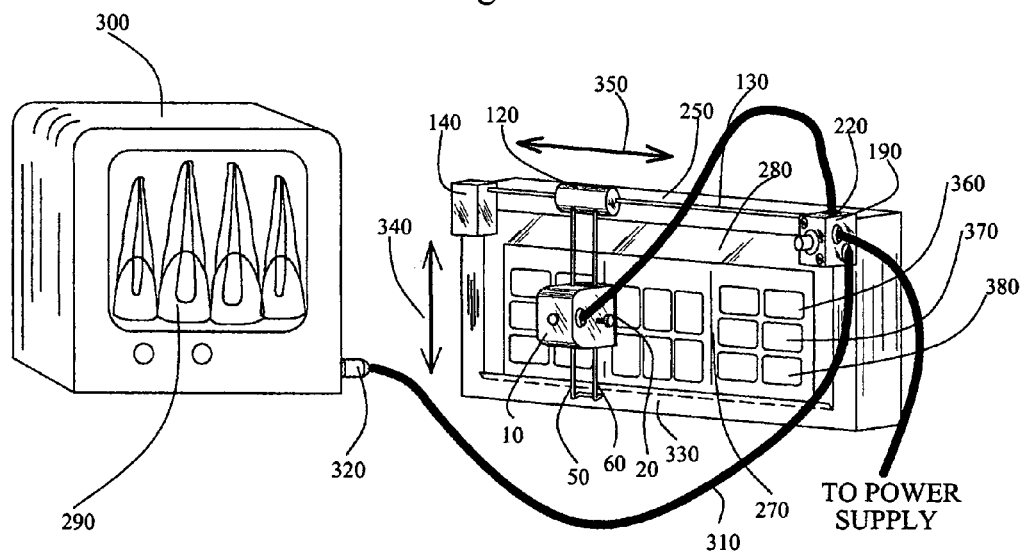
FIG. 2 is a view of the apparatus mounted on a standard dental x-ray viewer. Also shown is the video monitor with image thereon, transferred, via a video cable, through the high-resolution CCD video camera and the attachment housing.

Now refer to FIG. 2, which displays the apparatus of this disclosure mounted on x-ray viewer (250) with power switch (260). Target x-ray film set (270) is to be viewed by the operator. The operator can selectively move camera housing (10), with the CCD video camera mounted therein, in front of any individual film desired in a target film set, utilizing the movement allowed by camera housing (10) on the X-axis track (130) and Y-axis tracks (50) and (60). Light from fluorescent bulbs beneath translucent plate (280) will generally be too intense for the electronic iris of the CCD video camera, necessitating the use of a ruby-clear acrylic filter (20) over the lens opening. Image (290) from target film (270) is transferred to video monitor (300) via video cable (310) and RCA connector (320). Cross member (100) slides on a line configured to be parallel to the X-axis of translucent viewing plate (280) and target x-ray film (270), on viewer chassis (330), and acts, along with upper carrier (120), X-axis tracks (130), and Y-axis tracks (50) and (60), to hold said CCD video camera mounted inside camera chassis (10) in good focal length from target x-ray film (270). Arrow (340) displays the direction camera chassis (10) would follow when traveling parallel to the Y-axis of said target x-ray film. Arrow (350) displays the direction camera chassis (10) would travel if moving parallel to the X-axis of said target x-ray film.

Films (360), (370), and (380) demonstrate the different levels at which camera chassis (10) may be required to be selectively locked, by tightening locking knob (80). Camera chassis (10) is placed at the desired level and locking knob (80) is tightened against Y-axis track (60). Camera chassis (10), with CCD video camera mounted therein, may be moved in a direction parallel to the X-axis of target film (270), while locked on Y-axis tracks (50) and (60).

Figure 3:
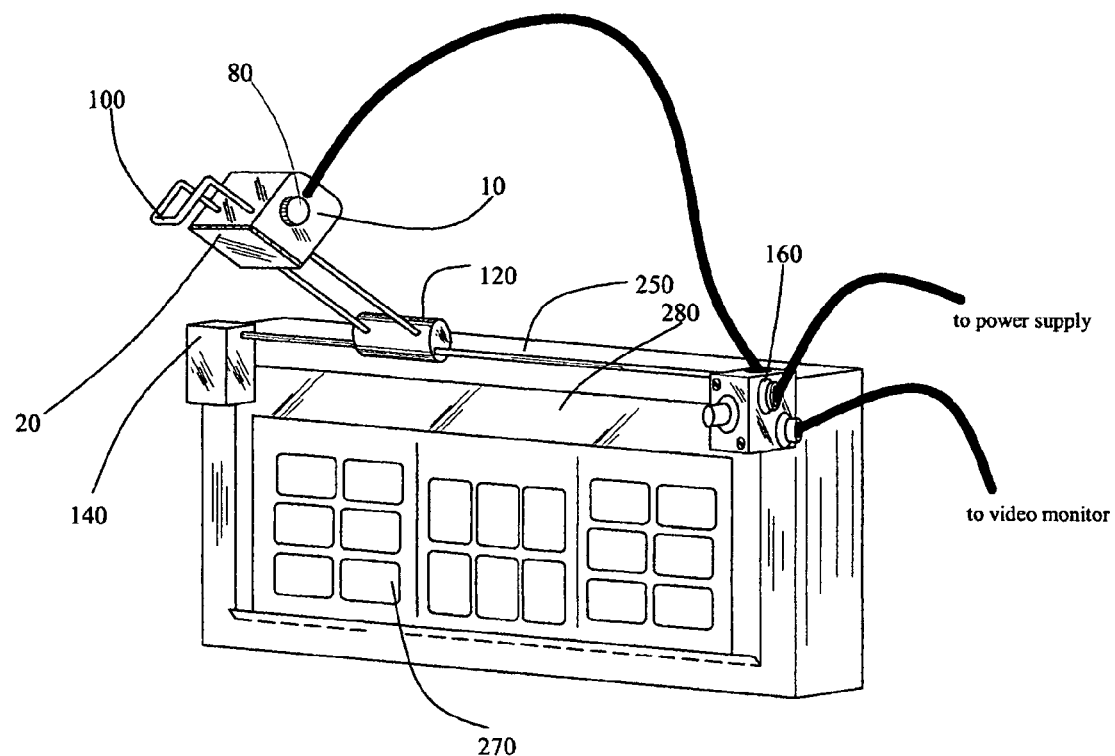
FIG. 3 is a view of the mounted apparatus rotated up and away from the x-ray viewer giving the operator an unobstructed view of the target x-ray films.

Now refer to FIG. 3 which demonstrates how camera chassis (10), with CCD video camera mounted therein, can be rotated upward on X track (130) which will allow the operator a full unobstructed view of target x-ray film (270).

Figure 4:
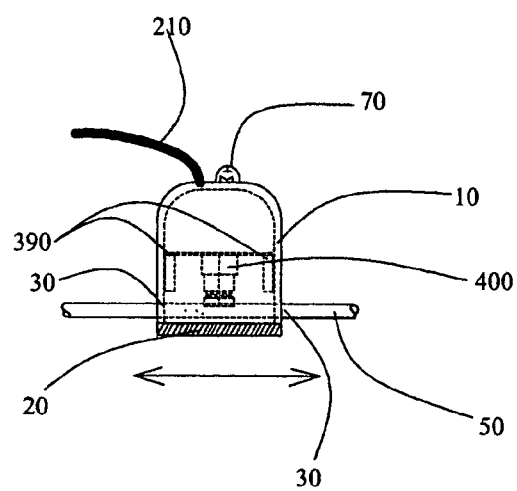
FIG. 4 is a side view of the camera housing showing the CCD video camera and mount, along with the ruby-clear acrylic filter.

Refer to FIG. 4 for the showing of camera chassis (10). There is provided video camera mounts (390) on which CCD video board camera (400) with lens is mounted. Cable (210) carries 12-volt DC power, and wire capable of carrying an analog video image. Due to its larger diameter, through hole (30) allows camera chassis (10) to move freely on the Y-axis track (50).

Figure 5:
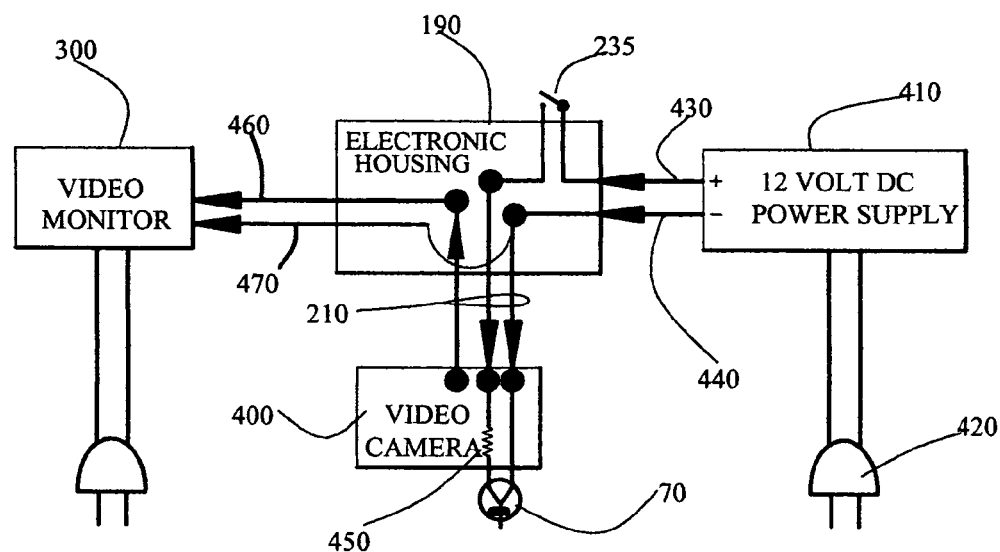
FIG. 5 is a schematic of the electronic circuitry of the present invention.

FIG. 5 is a schematic diagram of the circuitry of the present invention. Attachment housing (160) contains the confluence of all electronic couplers. Power supply (410) has 110 volt plug (420). Positive 12-volt DC cable (430) and negative 12-volt DC cable (440) are coupled with CCD video board camera (400), and LED indicator light (70) which requires resister (450) for reduction of voltage. Video lead (460) carries the x-ray video image from CCD video camera (400) to video monitor (300), again through attachment housing (160). Wire lead (470) carries 12 volt DC common.

Additional modifications and improvements of the present invention may be also apparent to those skilled in the art. Thus, the particular combination of parts described and illustrated herein is intended to represent only one embodiment of the invention and is not intended to serve as limitations of alternative devices within the spirit and scope of the invention.

What is claimed is:

1. An apparatus comprising:
(a) at least one attachment member configured so that the apparatus of this invention can be secured on the chassis of a standard dental x-ray viewer;
(b) at least one Y-axis track mechanism disposed so that it is parallel to the Y-axis of the plane of the translucent viewing plate of a standard dental x-ray viewer;
(c) a camera housing with one CCD video camera board with lens mounted therein, configured so that it is capable of sliding on said Y-axis track, and positioned in said apparatus so that a well focused image can be captured from a target x-ray film;
(d) at least one X-axis track mechanism disposed so that it is parallel to the X-axis of the plane of the translucent viewing plate of a standard dental x-ray viewer;
(e) at least one carrier configured to be slidably mounted on said X-axis track, and mechanically coupled with said Y-axis tracks;
(f) a locking mechanism capable of selectively locking said camera housing on said Y-axis track;
(g) a housing configured to accept video and power leads from said CCD video camera;
(h) a cable capable of carrying power leads to said CCD video camera;
(i) a cable capable of carrying video from said CCD video camera signals to an external monitor;
(j) a power supply capable of supplying power the said CCD video camera.

2. The apparatus of claim 1 wherein the current invention is configured to be mounted on the chassis of a standard dental x-ray viewer via said attachment member and via an attachment means, and to hold said CCD video camera in good focal length from target x-ray film.

3. The device of claim 1 wherein said X-axis tracks and said Y-axis tracks are configured in such a way that, when the apparatus of this invention is mounted on a standard dental x-ray viewer, said CCD video camera is movable so that all images of a target x-rays film set placed thereon are capable of being viewed on a monitor.

4. An analog x-ray image apparatus, configured to hold a moveable CCD video camera, which is capable being mounted on a standard dental x-ray viewer, and which is capable of capturing images from a set of dental x-ray film and sending said images to a monitor, comprising:
(a) at least one attachment member, that will allow the apparatus of this invention to be mounted on the chassis of a standard dental x-ray viewer via a mounting means;
(b) at least one Y-axis track mechanism, configured to be parallel to the Y-axis of the plane of the translucent plate of said standard dental x-ray film viewer and configured to be at least as long as the height of said translucent plate;
(c) a camera housing with a CCD video camera mounted therein, disposed to be moveable on said Y-axis track;

(d) at least one X-axis track mechanism configured to be parallel to the X-axis of the plane of the translucent viewing plate of a standard dental x-ray viewer, and configured in length so that said X-axis track will allow for the movement of said camera chassis, and said CCD video camera mounted therein, to view the entire length of dental x-ray film set placed on said translucent viewing plate;

(e) at least one carrier configured to be slidably mounted on said X-axis track, and mechanically coupled with said Y-axis tracks;

(f) a locking mechanism configured to selectively maintain said camera chassis, with said CCD video camera therein, stationary on said Y-axis track;

(g) a cable, with wires electronically coupled with a power source and said CCD video camera;

(h) a cable, with output video wires electronically coupled with said CCD video camera and an electronic monitor;

(i) a power supply capable of supplying power the said CCD video camera.

5. The apparatus of claim 4 wherein said attachment member comprises a housing that is capable of holding electronic couplings for the purpose of relaying power from said power supply to said CCD video camera.

6. The apparatus of claim 4 wherein said attachment member comprises a housing that is capable of holding electronic couplings for the purpose of transferring video signals to a video monitor from said CCD video camera.

7. The apparatus of claim 4 wherein said attachment member comprises an electronic housing that is capable of holding electronic couplings required to transfer video signals to a computer equipped to accept said video images.

* * * * *